July 29, 1975 A. J. BROWN, SR Plant Pat. 3,750
BEGONIA PLANT
Filed May 15, 1974
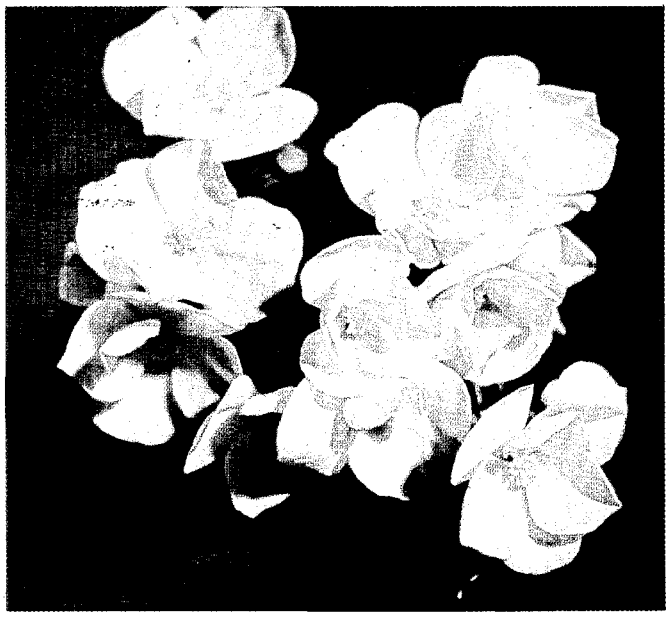

United States Patent

Plant Pat. 3,750
Patented July 29, 1975

3,750
BEGONIA PLANT

Andrew J. Brown, Sr., Cardiff, Calif., assignor to Mikkelsens Inc., Ashtabula, Ohio

Filed May 15, 1974, Ser. No. 470,024
Int. Cl. A01h *5/00*
U.S. Cl. Plt.—68 1 Claim

The present invention relates to a new and distinctive variety of begonia plant, known by the varietal name Browns Golden Gelbe and botanically known as *Begonia elatior* (B × *hiemalis-Fotsch*). The new cultivar was discovered by me as a mutation on a flowering crop of potted begonias of the parent cultivar Bernsteins Gelbe, disclosed in U.S. Plant Pat. No. 3,474, issued Feb. 12, 1974, in the name of Bruno Bernstein, and assigned to Mikkelsens Inc., Ashtabula, Ohio. The parent cultivar is in turn a mutation of the unpatented Rieger begonia variety known by the varietal name Locksorange. Asexual reproduction by stem and leaf cuttings has reproduced the unique features of the new variety through successive propagations.

The following characteristics distinguish the new begonia from both its parent and other begonias commercially known and use in the floriculture industry:

1. Differs from parent in having darker yellow tepals with slightly ruffled edges. Quite frequently five tepals rather than four.
2. Differs from parent in having deeper yellow colored anthers.
3. The new cultivar shows little if any outward symptoms when infected with the bacteria Xanthomonas when compared with Riegers Schwabenland varieties.
4. Is less resistant to powdery mildew than most of the Rieger *elatior* varieties.
5. Plant growth is slower although flowering time is the same as other Rieger types.
6. Leaf propagation of the new variety is one to two weeks faster than other Rieger begonias. The number of adventitious shoots developing averages five to seven.
7. The leaves of the new variety lack the sharp indentations of the Rieger Schwabenland types. Foliage coloring is lighter green with some infusion of red pigmentation. Leaves are less vigorous, not as thick or leathery as Schwabenland.
8. Flower color fading is less pronounced when compared to parent, with less pinking on the reverse side of tepals than in the parent.
9. Plant height is shorter than other Rieger types, measuring 20–26 cm.

The accompanying colored photograph illustrates the overall appearance of the new variety, showing the colors as true as it is reasonably possible to obtain in a colored reproduction of this type.

The following is a detailed description of the new begonia variety based on plants produced under commercial practices in Cardiff, Calif. and Ashtabula, Ohio. It will be understood that flower color, growth rate, etc. may vary significantly with varying environmental conditions such as daylength, temperature, and light intensity.

Color references are made to the Royal Horticultural Society Colour Chart except where general color terms of ordinary dictionary significance are used.

Parentage: Mutation from Bernsteins Gelbe, U.S. Plant Pat. No. 3,474.

Propagations: Continuous and successive propagation of both leaf cuttings and terminal stem cuttings have established stability of the new cultivar.

Rooting habit: Quite rapid, 15–20 days at 22° C., with adventitious shoots emerging in six to eight weeks under conditions at Cardiff, Calif. Roots are very fine.

Form: Upright.

Habit of growth: Slow, some self-branching, full body because of development of numerous underground shoots.

Blooming habits: Flowering initiates at numerous nodes; once initiated, flowering continues for an indefinite period of time. Holds up well as an outdoor plant in semi-shaded areas.

Blooming season: Normal blooming season is in mid-November. Controlled environment and starting with vegetative plants allows for year around flowering production.

Foliage: Small, heart shaped with very little indentations on leaf margins.

*Size.*—In comparison to Schwabenland Red leaf size of this new cultivar would be considered small, measuring five to seven cm. in diameter.

*Shape.*—Heart shaped tending to be oval.

*Texture.*—Top is smooth, glabrous; underside shiny.

*Margin.*—Near complete.

*Color.*—New foliage: upper side is green near 146A/B, underside is a light green/red. Mature foliage: upper side is green near 147A/B, underside is near 148–B.

Disease resistance: Less resistant to mildew. More tolerant to Xanthomonas.

Flowers:

*Borne.*—On continuous flowering trusses. Individual blooms last several weeks from the bud stage to senescence, with overall flowering continuing over several months.

*Quantity.*—10–15% more flowers than parent.

*Buds.*—In early stages are yellow 4–D, approximately 10–15 mm. in diameter, flat and round as a coin.

*Tepals.*—Inner two 13–A, outside two 12–A–B. Quite frequently flowers have five tepals as compared to four in the parent variety. Tepals are not perfectly flat but have a center ridge protruding to the backside and running from tip to flower stem. Edges of tepals are slightly ruffled.

*Reproductive organs.*—Stamens and anthers are yellow 17–B. Pollen—Yellow 12–C. Styles/ovaries—None seen to date.

I claim:

1. A new and distinct cultivar of *Begonia elatior* characterized particularly when compared to the present cultivar Bernsteins Gelbe by its darker yellow tepals with slightly ruffled edges; by the frequent occurrence of five tepals rather than four; its deeper yellow anthers; slower plant growth; faster leaf propagation; less flower color fading, with less pinking of the reverse side of the tepals, and by its shorter plant height.

No references cited.

ROBERT E. BAGWILL, Primary Examiner